(12) United States Patent
Moskal

(10) Patent No.: US 10,520,568 B2
(45) Date of Patent: Dec. 31, 2019

(54) HYBRID TOF-PET/MRI TOMOGRAPH

(71) Applicant: UNIWERSYTET JAGIELLONSKI, Cracow (PL)

(72) Inventor: Pawel Moskal, Czulowek (PL)

(73) Assignee: UNIWERSYTET JAGIELLONSKI, Cracow (PL)

(*) Notice: Subject to any disclaimer, the term of this patent is extended or adjusted under 35 U.S.C. 154(b) by 718 days.

(21) Appl. No.: 14/915,259

(22) PCT Filed: Aug. 29, 2014

(86) PCT No.: PCT/EP2014/068373
§ 371 (c)(1),
(2) Date: Feb. 29, 2016

(87) PCT Pub. No.: WO2015/028603
PCT Pub. Date: Mar. 5, 2015

(65) Prior Publication Data
US 2016/0209483 A1    Jul. 21, 2016

(30) Foreign Application Priority Data
Aug. 30, 2013   (PL) .......................... 405184

(51) Int. Cl.
*G01R 33/48* (2006.01)
*A61B 6/00* (2006.01)
(Continued)

(52) U.S. Cl.
CPC ............ *G01R 33/481* (2013.01); *A61B 6/037* (2013.01); *A61B 6/4417* (2013.01);
(Continued)

(58) Field of Classification Search
CPC ........ G01R 33/00; G01R 33/481; G01T 1/00; A61B 6/00
See application file for complete search history.

(56) References Cited

U.S. PATENT DOCUMENTS 4,864,131 A    9/1989  Rich et al.
4,939,464 A *  7/1990  Hammer ............. G01R 33/481
                                           250/363.03
(Continued)

FOREIGN PATENT DOCUMENTS

| WO | 2006119085 | 11/2006 |
| WO | 2007117801 | 10/2007 |
| WO | 2012135725 | 10/2012 |

OTHER PUBLICATIONS

C.P. Swann et al. "Lifetime of the First Excited State of N14" Physical Review, vol. 121, Issue 1, pp. 242-245, Jan. 1, 1961 XP002733766.
(Continued)

Primary Examiner — Luther Behringer
Assistant Examiner — Sean D Mattson
(74) Attorney, Agent, or Firm — Mark M. Friedman

(57) ABSTRACT

A hybrid tomograph that includes a chamber for examining an object, a TOF-PET tomograph and an MRI tomograph. The MRI tomograph has a magnet for producing a magnetic field and a receiving-transmitting coil. The TOF-PET tomograph has polymer scintillation strips to transmit scintillation photons outside the magnet of the MRI tomograph and outside the chamber of the hybrid TOF-PET/MRI tomograph. The polymer scintillation strips are arranged circumferentially inside the magnetic field produced by the magnet of the MRI tomograph. Photoelectric converters for converting light signals from the polymer scintillation strips to electrical signals are arranged outside the magnet of the MRI tomograph and outside the chamber of the hybrid TOF-PET/MRI tomograph.

13 Claims, 3 Drawing Sheets

(51) Int. Cl.
  *G01T 1/203* (2006.01)
  *G01T 1/29* (2006.01)
  *G01T 1/16* (2006.01)
  *A61B 6/03* (2006.01)

(52) U.S. Cl.
  CPC ............ *G01T 1/1603* (2013.01); *G01T 1/203* (2013.01); *G01T 1/2985* (2013.01)

(56) References Cited

U.S. PATENT DOCUMENTS

| | | | |
|---|---|---|---|
| 7,218,112 B2 | 5/2007 | Ladebeck et al. | |
| 8,013,607 B2 | 9/2011 | Demeester et al. | |
| 2005/0104001 A1 | 5/2005 | Shah | |
| 2007/0102641 A1* | 5/2007 | Schmand | G01R 33/26 250/363.03 |
| 2008/0214927 A1* | 9/2008 | Cherry | G01R 33/481 600/411 |
| 2008/0284428 A1* | 11/2008 | Fiedler | G01R 33/28 324/307 |
| 2010/0219347 A1* | 9/2010 | Schulz | G01T 1/1603 250/363.04 |
| 2012/0112079 A1* | 5/2012 | Moskal | G01T 1/2985 250/363.03 |

OTHER PUBLICATIONS

Pawel Moskal et al. "TOF-PET detector concept based on organic scintillators" Nuclear Medicine Review 2012 [online] vol. 15, No. C. Dec. 31, 2012, pp. C81-C84, XP002733765.

Daniel W. Rickey et al. "On Lifing the Inherent Limitations of Positron Emission Tomography by Using Magnetic Fields (MagPET)" Automedica, Gordong and Breach Science Publishers, London, GB. vol. 14, Jan. 10, 1992, pp. 355-369. XP007922936. ISSN: 0095-0963.

Zaidi H et al. "Design and Performance evaluation of a whole-body Ingenuity TF PET/ MRI system" Phys Med Biol. May 21, 2011; 56(10): 3091-3106.

P K Marsden et al. "Simultaneous PET and NMR" Br J Radiol. Nov. 2002;75 Spec No. S53-9.

Harald H. Quick "Whole-Body MR/PET Hybrid Imaging:Technical Considerations, Clinical Workflow, and Initial Results" Magnetom Flash Jan. 2011 www.siemens.com/magnetom-world.

* cited by examiner

HYBRID TOF-PET/MRI TOMOGRAPH

TECHNICAL FIELD

The present disclosure relates to a hybrid TOF-PET/MRI tomograph, comprising a TOF-PET tomograph and an MRI tomograph.

BACKGROUND

Images of the interiors of bodies may be acquired using various types of tomographic techniques, which involve recording and measuring radiation from tissues and processing acquired data into images.

One of these tomographic techniques is positron emission tomography (PET), which involves determining spatial distribution of a selected substance throughout the body and facilitates detection of changes in the concentration of that substance over time, thus allowing to determine the metabolic rates in tissue cells.

The selected substance is a radiopharmaceutical administered to the examined object (e.g. a patient) before the PET scan. The radiopharmaceutical, also referred to as an isotopic tracer, is a chemical substance having at least one atom replaced by a radioactive isotope, e.g. $^{11}C$, $^{15}O$, $^{13}N$, $^{18}F$, selected so that it undergoes radioactive decay including the emission of a positron (antielectron). The positron is emitted from the atom nucleus and penetrates into the object's tissue, where it is annihilated in reaction with an electron present within the object's body.

The phenomenon of positron and electron annihilation, constituting the principle of PET imaging, consists in converting the masses of both particles into energy emitted as annihilation photons, each having the energy of 511 keV. A single annihilation event usually leads to formation of two photons that diverge in opposite directions at the angle of 180° in accordance with the law of conservation of the momentum within the electron-positron pair's rest frame, with the straight line of photon emission being referred to as the line of response (LOR). The stream of photons generated in the above process is referred to as gamma radiation and each photon is referred to as gamma quantum to highlight the nuclear origin of this radiation. The gamma quanta are capable of penetrating matter, including tissues of living organisms, facilitating their detection at certain distance from object's body. The process of annihilation of the positron-electron pair usually occurs at a distance of several millimetres from the place of the radioactive decay of the isotopic tracer. This distance constitutes a natural limitation of the spatial resolution of PET images to a few millimetres.

A PET scanner comprises detection devices used to detect gamma radiation as well as electronic hardware and software allowing to determine the position of the positron-electron pair annihilation on the basis of the position and time of detection of a particular pair of the gamma quanta. The radiation detectors are usually arranged in layers forming a ring around object's body and are mainly made of an inorganic scintillation material. A gamma quantum enters the scintillator, which absorbs its energy to re-emit it in the form of light (a stream of photons). The mechanism of gamma quantum energy absorption within the scintillator may be of dual nature, occurring either by means of the Compton's effect or by means of the photoelectric phenomenon, with only the photoelectric phenomenon being taken into account in calculations carried out by current PET scanners. Thus, it is assumed that the number of photons generated in the scintillator material is proportional to the energy of gamma quanta deposited within the scintillator.

When two annihilation gamma quanta are detected by a pair of detectors at a time interval not larger than several nanoseconds, i.e. in coincidence, the position of annihilation position along the line of response may be determined, i.e. along the line connecting the detector centres or the positions within the scintillator strips where the energy of the gamma quanta was deposited. The coordinates of annihilation place are obtained from the difference in times of arrival of two gamma quanta to the detectors located at both ends of the LOR. In the prior art literature, this technique is referred to as the time of flight (TOF) technique, and the PET scanners utilizing time measurements are referred to as TOF-PET scanners. This technique requires that the scintillator has time resolution of a few hundred picoseconds.

Another method of imaging is MRI (Magnetic Resonance Imaging), which uses the magnetic properties of atomic nuclei, in particular, nuclei of hydrogen atoms, that is protons widely occurring in matter, including tissues of living organisms. The MRI technique allows obtaining images of the density distribution of hydrogen atoms giving the morphological image of tissues.

Superimposing of a functional image (PET) over a morphological image (MRI) considerably increases the capabilities of imaging techniques: a PET image enables precise positioning of metabolic changes in individual organs and the determination of the degree of these changes, whereas the obtainment of an MRI image at the same time allows a precise allocation of these changes to respective organs. Obtained hybrid PET/MRI images may be useful in scientific research on physiological processes, where it is especially important to precisely assign to respective tissues metabolic changes of tested radiopharmaceuticals, during imaging.

Today, in many laboratories in the world, technology that would allow for simultaneous PET and MRI imaging is intensively developed. Known PET/MRI hybrid tomographs are devices in which the PET tomograph and the MRI tomograph are spatially separated. The main difficulty in combining the two imaging techniques is due to mutual interruption of signals between PET and MRI detection systems. Strong magnetic fields used in MRI interfere with operation of converters of light impulses into electrical impulses as well as they disturb transmission and processing of the signals in PET detectors. Such design of a device causes that PET and MRI imaging is, in fact, carried out in different places of object's body and at different time—the object is moved incrementally between successive imaging, thus it is required to move the object and to stop him between successive imaging. This procedure involves a threat that image distortions, so-called artefacts, may occur, especially in abdominal cavity organs, which may move between individual scanning events due to accelerations to which the object is subjected during shifting. Moreover, the superimposing of MRI and PET images, taken at different times, over each other, requires that additional corrections should be introduced due to the weakening activity of the radiopharmaceutical and metabolic processes; what also needs to be remembered is that each of these corrections is additionally exposed to systemic errors that occur when the images are superimposed. In turn, inserting a PET tomograph between coils of MRI tomograph and the object distorts the magnetic fields and reading of electromagnetic signals of the MRI tomograph due to eddy currents and electromagnetic waves induced in the electronics components used for reading and transmission of electrical signals of PET tomograph.

The state of the art technology tried to overcome the above mentioned problems and it describes equipment enabling simultaneous PET and MRI diagnostics.

A U.S. Pat. No. 8,013,607 discloses a solution wherein PET and MRI tomographs are spatially separated and aligned in close proximity to each other. The device allows sequential PET and MRI scans and the object, during the examination, is placed on the platform and moved between the tomographs. A similar solution was also described in the article "Design and performance evaluation of a whole-body Ingenuity TF PET/MRI system" (Z. Zaidi et al. Phys Med. Biol. 56 (2011), pp. 3091-3106). The disclosed technique avoids the technical difficulties related to the negative impact of PET detectors on magnetic fields and MRI electromagnetic signals through the physical separation of the two detectors. However, moving the object between individual imaging can lead to distortion in superimposed PET and MRI images (so-called artefacts), especially in the case of abdominal organs, which can move between the individual scanning activities as a result of acceleration experienced by the object when moving.

The article "Simultaneous PET and NMR" (P K Marsden et al. Brit J Radiology 75 (2002) pp. 53-59), describes a hybrid tomograph with non-standard readout by carrying signals over long optical fibres, which are inserted inside the MRI scanner. However, the use of this solution reduces the imaging field of view and PET imaging quality deteriorates due to the need for signals to be transmitted in several-metre thin optical fibres.

The article "Whole-Body MR/PET Hybrid Imaging: Technical Considerations, Clinical Workflow, and Initial Results" (Quick H. et al., MAGNETOM Flash January/2011 pp. 88-100) presents the possibility of using silicon photomultipliers or avalanche diodes instead of the standard photomultiplier tubes, and enclosing them along with electronics in an electromagnetic housing made, for example, of copper and inserting them between the gradient coil and the signal-readout coil of MRI tomograph. A similar solution consisting in using silicon photomultipliers is also disclosed in the patent description U.S. Pat. No. 7,218,112. The described method allows simultaneous imaging in a relatively large transverse field of view. This solution is schematically illustrated in FIG. 1, in which the PET 20 detectors are located between the receiving-transmitting coils 31 surrounding the object 5 and the gradient coils 32. PET detectors are made of LSO crystals 21 with an avalanche photodiode matrix 22 integrated with a cooling system 23 and analogue readout electronics 24. Detection modules have shields made of copper. Such a layout of PET and MRI tomograph elements can, however, lead to distortions of magnetic fields and electromagnetic signals used in MRI and distortions of signals in PET tomograph. The main factors causing the disorders described above are: (i) converters, electronics and cooling systems, which are, as per the solution, between the receiving-transmitting coils and gradient coils, (ii) transmission of electrical signals from PET detectors between the receiving-transmitting coils and gradient coils, (iii) scattering of annihilation quanta in the receiving-transmitting MRI coils located between the object and the layer of PET detectors. Furthermore, the presented solution is expensive, and the cost of the detector and electronics increases approximately linearly with the length of the longitudinal field of view, which is a significant limitation preventing large-scale production of hybrid PET/MRI tomographs with a large longitudinal field of view.

A US patent application US20120112079 describes a strip device and the method used in the determination of position and time of gamma quanta reaction, and the application of this device in PET. The TOF-PET tomograph, described in the application, allows simultaneous imaging of the whole object's body, while the material used to register gamma quanta is polymers doped with elements of high atomic numbers. The device described in this application reduces the cost of PET tomography. US20120112079 does not present, however, a method for simultaneous PET and MRI imaging using polymer scintillator strips.

A PCT application WO2006119085 discloses an integrated PET-MRI scanner. This integrated scanner includes a main magnet that generates a magnetic field, wherein images of the subject is generated in a central region of the magnetic field. It also includes a PET scanner which is enclosed by the main magnet. The PET scanner further comprises: at least one ring of scintillators, which is situated in the central region of the magnetic field and, one or more photodetectors, which are coupled to the ring of scintillators, so that the one or more photodetectors are outside the central region of the magnetic field. The integrated scanner also includes radio frequency (RF) coils which are enclosed by the PET scanner. By keeping the photodetectors and associated circuitry outside the central region of the magnetic field, the integrated scanner reduces the electromagnetic interference (EMI) between the PET scanner and the MRI scanner. The gamma scintillators are positioned only in the central region of the magnetic field and the photoelectric converters are positioned in the working area of the MRI scanner. The scintillators are made from crystals: LSO, BGO.

It would be desirable to provide an imaging device utilizing polymer scintillators, which would enable simultaneous registration of gamma radiation and execution of nuclear magnetic resonance with a large field of view, enabling the elimination of any artefacts that could distort the image due to the movement of the object, and systematic errors formed during superimposure of images made at various positions and times. This will allow effective, simultaneous functional and morphological imaging.

SUMMARY

There is presented a hybrid TOF-PET/MRI tomograph comprising a TOF-PET tomograph and an MRI tomograph, wherein the TOF-PET tomograph comprises polymer scintillation strips arranged circumferentially inside the working area of the magnetic field of the receiving-transmitting coil of the MRI tomograph and photoelectric converters for converting light signals from the scintillation strips to electrical signals, wherein the photoelectric converters are arranged outside the working area of magnetic field of the MRI tomograph.

Preferably, the position of TOF-PET tomograph is fixed with respect to the MRI tomograph during operation of the hybrid tomograph.

Preferably, the receiving-transmitting coil of the tomograph is positioned directly at the layer of gamma radiation scintillators at the outside of the hybrid tomograph.

Preferably, the scintillation strips are arranged circumferentially, forming a ring, such that the longest edges of the strips are parallel to the longitudinal axis of the hybrid tomograph.

Preferably, the polymer scintillation strips are adjacent to each other.

Preferably, the polymer scintillation strips are separated with respect to their longest edges.

Preferably, each polymer scintillation strip is connected to at least two photoelectric converters.

Preferably, the photoelectric converters are photomultiplier tubes.

Preferably, the photoelectric converters are avalanche diodes.

Preferably, the photoelectric converters are silicon photomultipliers.

Preferably, the TOF-PET tomograph and the MRI tomograph are connected to a common clock signal.

Preferably, the tomograph is configured for simultaneous TOF-PET and MRI imaging.

Preferably, the tomograph is configured for sequential TOF-PET and MRI imaging.

BRIEF DESCRIPTION OF FIGURES

Example embodiments are presented on a drawing wherein.

DETAILED DESCRIPTION

The numerals in the figures are used to indicate:
101—TOF-PET/MRI hybrid tomograph; 120—TOF-PET tomograph; 121—polymer scintillation strips; 122—photoelectric converter; 123—photoelectric converters magnetic shields; 130—MRI tomograph; 131—layer of receiving-transmitting coils; 132—magnets that produce a static magnetic field $B_0$, coil magnets producing gradient field, cooling system; 104—chamber of the hybrid TOF-PET/MRI tomograph to examine the object; 105—object; 106—platform for placing the object into the chamber of the hybrid TOF-PET/MRI tomograph; 107—longitudinal axis of the hybrid tomograph; 108—magnetic field lines.

Figure 1:
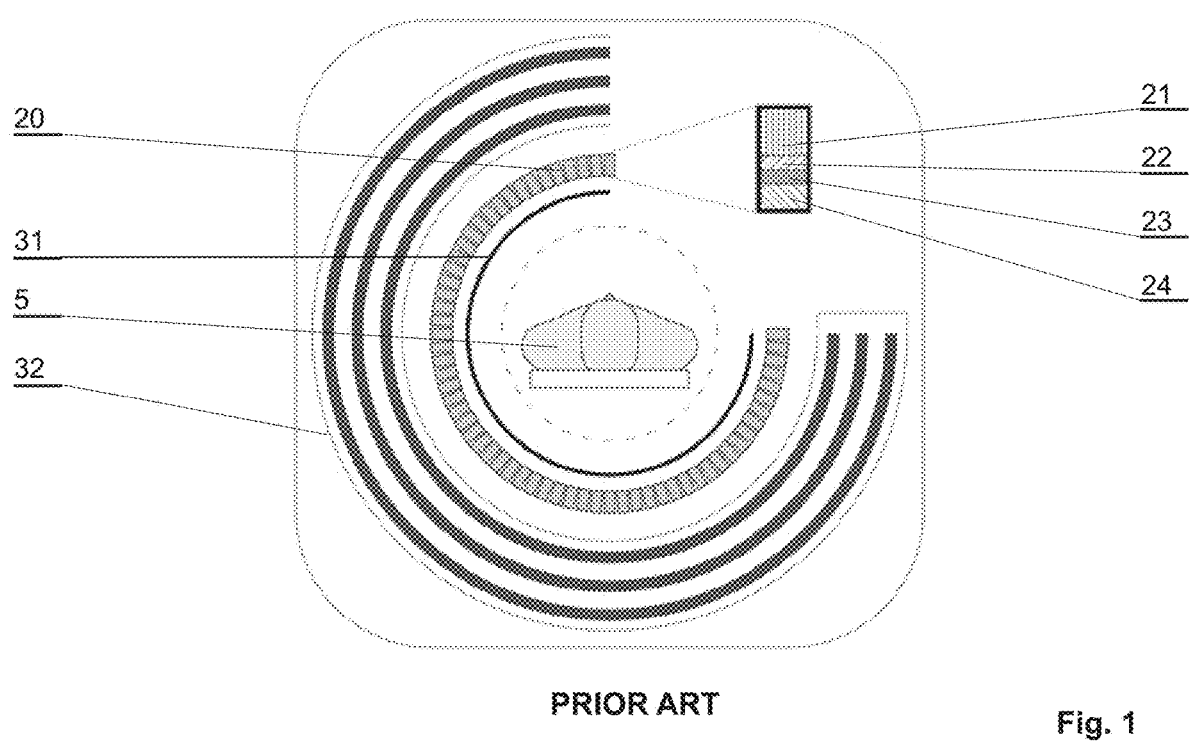
FIG. 1 shows a prior art PET/MRI hybrid tomograph.
Figure 2:
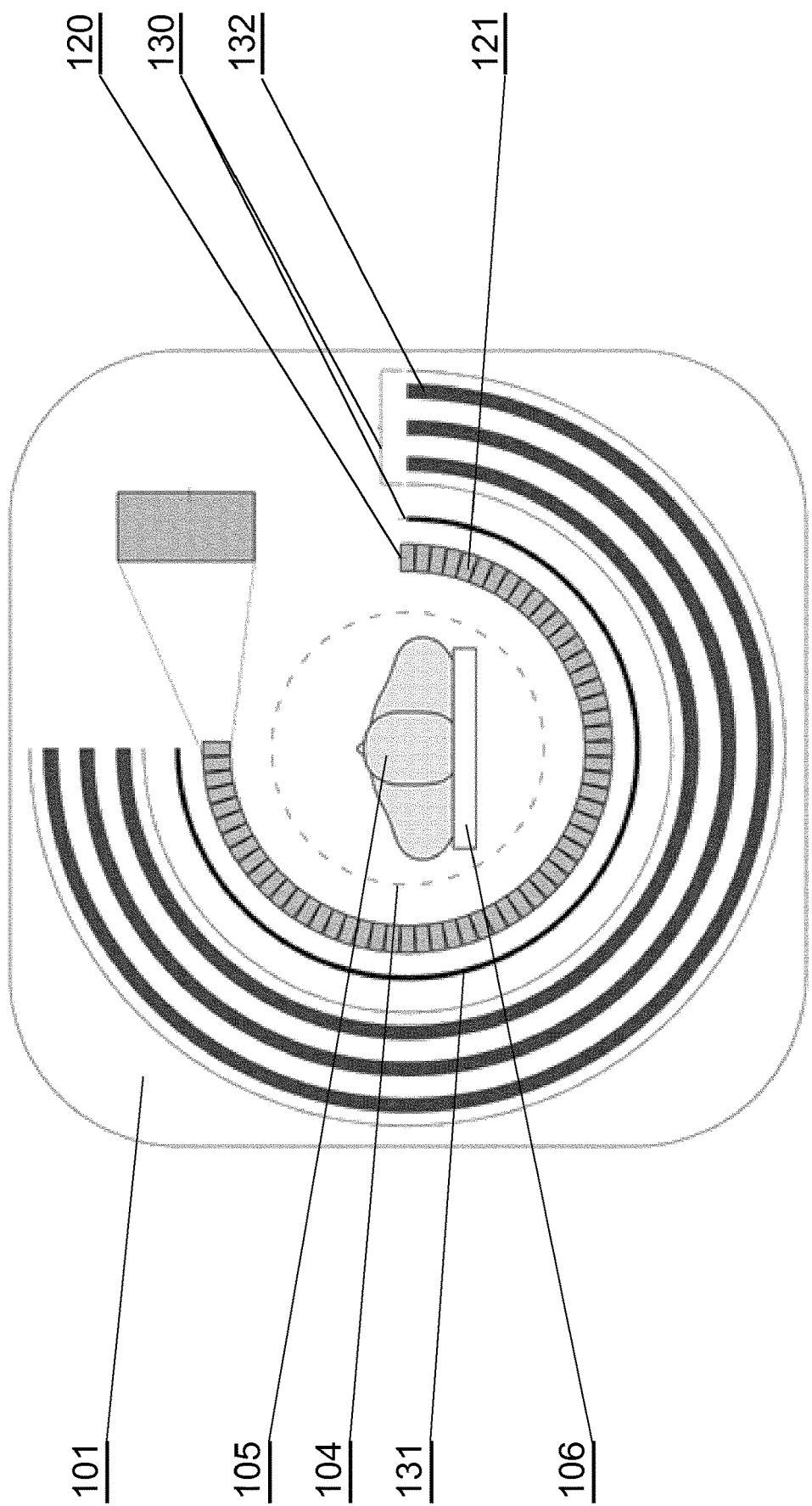
FIG. 2 illustrates schematically a new TOF-PET/MRI hybrid tomograph.

FIG. 2 illustrates schematically a hybrid tomograph 101 which has a chamber 104, into which the object 105 is introduced after administration of the radiopharmaceutical. In order to perform the examination, the object is placed on the platform 106, wherein after reaching a predetermined position in the chamber 104, the position of the platform 106 remains constant until the end of the examination.

Tomograph 101 includes two different types of tomographs: TOF-PET tomograph 120 and MRI tomograph 130. TOF-PET tomograph 120 constitutes the inner layer of hybrid tomograph 101 and registers gamma radiation during operation of the tomograph 101

The inner layer of the TOF-PET tomograph 120 is filled with nonmagnetic polymer scintillation strips 121, which, in the preferred embodiment, are admixed with atoms having an atomic number of at least fifty; the strips have low density and a thickness of, e.g. 2 cm, and they do not interfere with magnetic fields and electromagnetic waves used in MRI tomography. Strips 121 can be placed circumferentially, spaced apart at predetermined distance or they may adjoin each other along their longest edges to form an elongated, cylindrical ring (or another shape) coaxial with the longitudinal axis 107 of the hybrid tomograph 101. The gamma quanta resulting from the decay of the radioisotope, when reaching the strips 121 are converted into light impulses by scintillator material 121 and then they are transported to the photoelectric converters 122. The strip design of the tomograph PET 120 allows not only the use of polymer scintillators as the detection layer, but also as a system of light guides used for transporting light pulses outside the magnet MRI 132

The MRI tomograph 130 constitutes the outer layer of hybrid tomograph 101 and registers electromagnetic waves during operation of the tomograph. The MRI tomograph 130 may be a conventional MRI tomograph, whose construction and operation are known in the state of the art. For example, the MRI tomograph 130 may comprise a layer of receiving-transmitting coils 131 immediately surrounding the layer of detector PET 120 and magnets generating a static magnetic field $B_0$, coil magnets producing gradient field, cooling system and housing, jointly referred to as 132 in FIG. 2, in order to achieve greater clarity.

Figure 3:
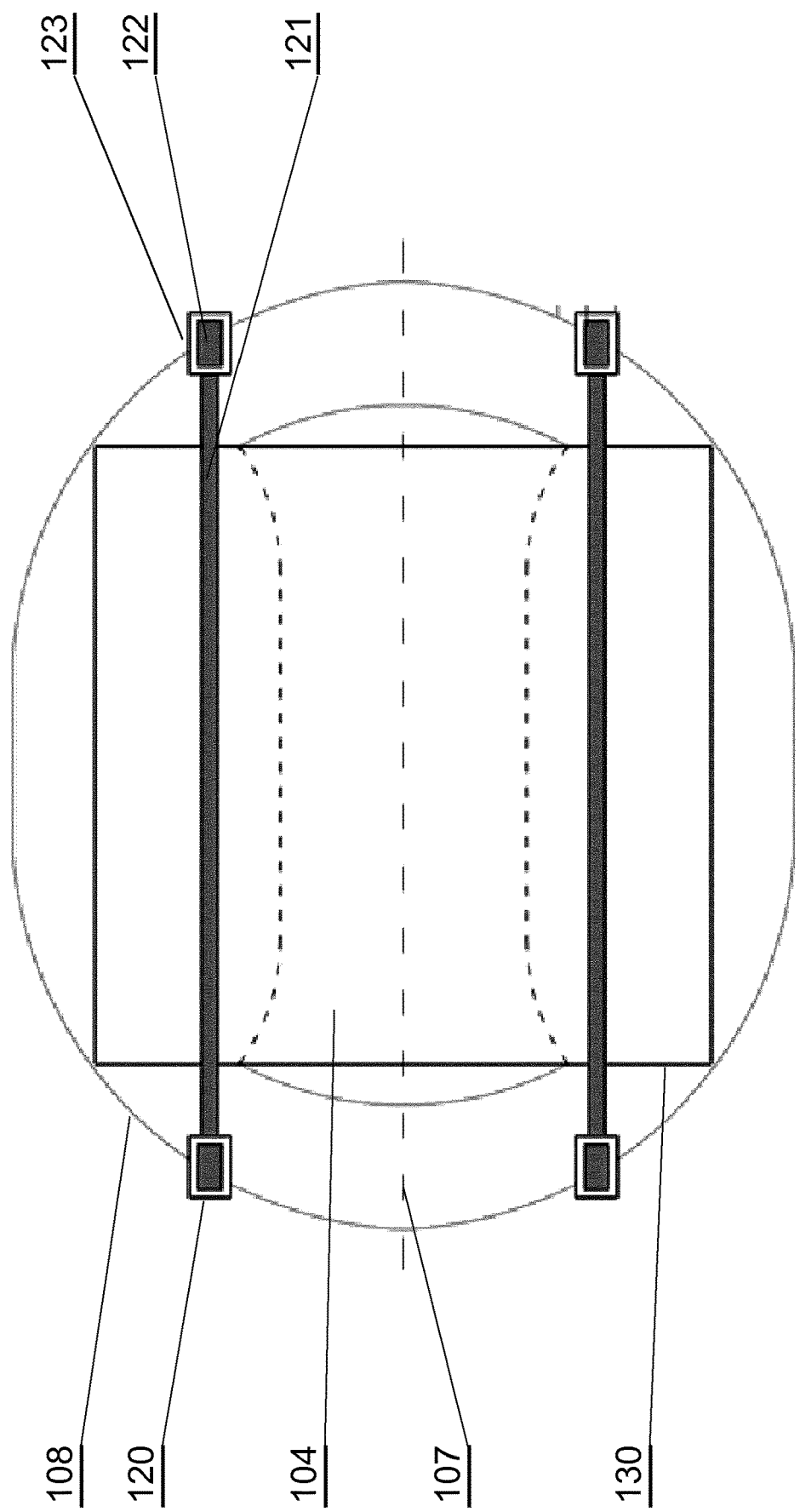
FIG. 3 illustrates schematically a new TOF-PET/MRI hybrid tomograph in a plane comprising the longitudinal axis of the tomograph.

FIG. 3 is a sectional view of a hybrid tomograph 101 in a plane comprising the longitudinal axis 107 of the tomograph. Each scintillation strip 121 of the TOF-PET 120 detector can be optically connected with two photoelectric converters 122. Converters 122 are provided outside the working area of the receiving-transmitting coil 131 of MRI tomograph 130. Converters can be placed in the magnetic shields 123, for example of "miu-metal", and the photoelectric converters can be any known converters, for example: avalanche diodes, silicon photomultipliers, and even ordinary photomultiplier tubes, depending on the expected time resolution, wherein using a photomultiplier tube gives the best TOF resolution, not available in current TOF-PET/MRI tomographs.

Functional imaging using PET and MRI detectors by means of TOF-PET/MRI tomograph can be performed simultaneously or sequentially, wherein the sequential imaging can be made according to the desired sequence or, depending on the needs of imaging, it can also be performed only with PET detectors or using only MRI detectors.

Data collected during imaging using both tomographs can be recorded along with a time stamp synchronised with a common clock, which enables superimposition of PET and MRI images performed at the same intervals. Data acquisition and subsequent PET and MRI images reconstruction procedures can be based on solutions known in the state of the art.

With properly designed configuration of gamma radiation detectors, in which the photoelectric converters 122 are provided outside a magnet of MRI tomograph, the hybrid tomograph presented herein enables simultaneous operation of PET and MRI tomographs without causing distortion of the magnetic field and electromagnetic waves of MRI tomograph.

Development of a hybrid tomograph with the possibility of conducting simultaneous registration of gamma radiation and MRI imaging was possible thanks to the use of light-guiding properties of non-magnetic polymer scintillator strip and the use of the strips for transmission of photons outside the magnetic field.

Moreover, such a solution made it possible to provide a hybrid tomograph, wherein in the imaging area there are only non-magnetic materials of TOF-PET detector, allowing for placing—with respect to conventional hybrid PET/MRI tomographs—of receiving-transmitting coils of MRI tomograph outside gamma radiation detectors, thanks to which annihilation radiation emitted by the object in the hybrid tomograph presented herein is not attenuated by transmitting-receiving coils of MRI tomograph and other elements of this system, and may reach directly the gamma radiation detector. The non-magnetic detection layer of TOF-PET is thus, at the same time, material for registering annihilation quanta and to transmit signals outside magnets of MRI tomograph, where they are processed by electronic converters and electronics shielded against residual fringe field.

It should be emphasized that the use of polymer strip gamma radiation detectors further allowed increasing the longitudinal field of view of the TOF-PET/MRI tomograph relative to other known devices of this type. Detection strips of the PET tomograph can be placed along the entire length of the MRI tomograph—in the inner layer, making it possible to carry out imaging of the entire object at the same time without having to move the object or detectors; thus, any artefacts and systematic errors can be eliminated.

In addition, the described design of the tomograph allows the use of any of the known photoelectric converters, allowing selection of photoelectric converters of high resolution for the tomograph presented herein in order to obtain precise hybrid PET/MRI images.

While the technical solutions presented herein have been depicted, described, and defined with reference to particular preferred embodiment(s), such references and examples of implementation in the foregoing specification do not imply any limitation on the invention. Various modifications and changes may be made thereto without departing from the scope of the technical solutions presented. The presented embodiments are given as example only, and are not exhaustive of the scope of the technical solutions presented herein. Accordingly, the scope of protection is not limited to the preferred embodiments described in the specification, but is only limited by the claims that follow.

The invention claimed is:

1. A hybrid TOF-PET/MRI (Time-Of-Flight Positron Emission Tomography/Magnetic Resonance Imaging) tomograph comprising:
    a chamber for examining an object,
    an MRI tomograph comprising a magnet for producing a magnetic field and a receiving-transmitting coil, wherein the magnet surrounds the chamber for examining the object and defines a magnet-surrounded volume and
    a TOF-PET tomograph comprising polymer scintillation strips, wherein at least one of the polymer scintillation strips is arranged partially inside the magnet-surrounded volume and partially outside the magnet-surrounded volume, to transmit scintillation photons outside the magnet-surrounded volume and outside the chamber of the hybrid TOF-PET/MRI tomograph, the polymer scintillation strips being arranged circumferentially inside the magnetic field produced by the magnet of the MRI tomograph; and photoelectric converters for converting light signals from the polymer scintillation strips to electrical signals, wherein the photoelectric converters are arranged outside the magnet-surrounded volume and outside the chamber of the hybrid TOF-PET/MRI tomograph.

2. The hybrid TOF-PET/MRI tomograph according to claim 1, wherein a position of the TOF-PET tomograph is fixed with respect to a position of the MRI tomograph.

3. The hybrid TOF-PET/MRI tomograph according to claim 1, wherein the polymer scintillation strips are arranged circumferentially and form a ring, such that longest edges of the polymer scintillation strips are parallel to a longitudinal axis of the hybrid TOF-PET/MRI tomograph.

4. The hybrid TOF-PET/MRI tomograph according to claim 3, wherein the polymer scintillation strips are adjacent to each other along their longest edges and coaxial with the longitudinal axis of the hybrid tomograph.

5. The hybrid TOF-PET/MRI tomograph according to claim 3, wherein the polymer scintillation strips are spaced apart with respect to their longest edges.

6. The hybrid TOF-PET/MRI tomograph according to claim 3, wherein the receiving-transmitting coil of the MRI tomograph is positioned outside the ring formed by the polymer scintillation strips, and adjacent to the polymer scintillation strips.

7. The hybrid TOF-PET/MRI tomograph according to claim 1, wherein each of the polymer scintillation strips is connected to two photoelectric converters.

8. The hybrid TOF-PET/MRI tomograph according to claim 1, wherein the photoelectric converters are photomultiplier tubes.

9. The hybrid TOF-PET/MRI tomograph according to claim 1, wherein the photoelectric converters are avalanche diodes.

10. The hybrid TOF-PET/MRI tomograph according to claim 1, wherein the photoelectric converters are silicon photomultipliers.

11. The hybrid TOF-PET/MRI tomograph according to claim 1, wherein the TOF-PET tomograph and the MRI tomograph are connected to a common clock signal.

12. The hybrid TOF-PET/MRI tomograph according to claim 1, wherein the hybrid TOF-PET/MRI tomograph is configured for simultaneous TOF-PET and MRI imaging.

13. The hybrid TOF-PET/MRI tomograph according to claim 1, wherein the hybrid TOF-PET/MRI tomograph is configured for sequential TOF-PET and MRI imaging.

* * * * *